United States Patent [19]
Schläpfer et al.

[11] Patent Number: 6,059,829
[45] Date of Patent: May 9, 2000

[54] INTERVERTEBRAL IMPLANT

[75] Inventors: Fridolin Schläpfer, Glarus; Martin Hess, Hölstein, both of Switzerland

[73] Assignee: Synthese, Paoli, Pa.

[21] Appl. No.: 08/737,442

[22] PCT Filed: Mar. 8, 1995

[86] PCT No.: PCT/CH95/00051

§ 371 Date: Nov. 1, 1996

§ 102(e) Date: Nov. 1, 1996

[87] PCT Pub. No.: WO96/27348

PCT Pub. Date: Sep. 12, 1996

[51] Int. Cl.[7] .................................................. A61F 2/44
[52] U.S. Cl. ................... 623/17; 623/16; 606/61
[58] Field of Search .................... 623/16, 17, 18; 606/60, 61, 70–73

[56] References Cited

U.S. PATENT DOCUMENTS

| | | | |
|---|---|---|---|
| 4,484,570 | 11/1984 | Sutter et al. ............................. | 606/72 |
| 4,834,757 | 5/1989 | Brantigan ................................ | 623/17 |
| 4,878,915 | 11/1989 | Brantigan ................................ | 623/17 |
| 4,961,247 | 10/1990 | Ray et al. ................................ | 623/16 |
| 5,015,247 | 5/1991 | Michelson ............................... | 623/17 |
| 5,059,193 | 10/1991 | Kuslich ................................... | 606/61 |
| 5,147,402 | 9/1992 | Bohler et al. ........................... | 623/16 |
| 5,290,312 | 3/1994 | Kojimoto et al. ...................... | 623/17 |
| 5,390,683 | 2/1995 | Pisharodi ................................ | 623/17 |
| 5,458,638 | 10/1995 | Kuslich et al. ......................... | 623/17 |
| 5,522,899 | 6/1996 | Michelson ............................... | 623/17 |
| 5,554,191 | 9/1996 | Lahille et al. ........................... | 606/61 |
| 5,593,409 | 1/1997 | Michelson ............................... | 623/17 |
| 5,683,463 | 11/1997 | Godefrey et al. ....................... | 623/17 |
| 5,766,252 | 6/1998 | Henry et al. ............................ | 623/17 |
| 5,885,299 | 3/1999 | Winslow et al. ....................... | 606/61 |
| 5,888,224 | 3/1999 | Beckers et al. ......................... | 623/17 |
| 5,980,522 | 11/1999 | Koros et al. ............................ | 623/17 |

FOREIGN PATENT DOCUMENTS

| | | | |
|---|---|---|---|
| 94 07 806 U | 7/1994 | Germany ................................. | 623/17 |
| WO 92/14423 | 9/1992 | WIPO ...................................... | 623/17 |

*Primary Examiner*—Mickey Yu
*Assistant Examiner*—Tram A. Nguyen
*Attorney, Agent, or Firm*—Pennie & Edmonds LLP

[57] ABSTRACT

The present invention related to an implant (1) for an intervertebral space consists of a frame (2) which is closed at the sides but open without restriction at the top and bottom and provided with an anterior lead-in face (3) and a posterior manipulation face (4). The upper (5) and lower boundary (6) of the frame (2) is convex, so that the implant (1) has an overall lens shape in the midplane (8) of the frame (2) containing the longitudinal axis (7) of the implant (1). The inner cavity (15) which is open without restriction at the top and bottom can be filled with a compressible material. The posterior manipulation face (4) of the frame (2) is provided with an aperture (9) to allow the introduction of a compression element (10) with which the compressible material can be forced out of the inner cavity (15).

19 Claims, 3 Drawing Sheets

INTERVERTEBRAL IMPLANT

TECHNICAL FIELD

The invention relates to an implant, especially for insertion into a intervertebral space. Such implants are primarily intended to promote bone bridges on vertebral bodies, and they are attached between the vertebral body and the spinal column after resection of a disk or intervertebral disk.

BACKGROUND ART

It is known that a damaged intervertebral disk can be removed, and that the resulting space can be filled with cortico-spongious bone.

In this method, the vertebral bodies are first stretched apart as much as possible by means of spreaders. A special technique consists in inserting wedge-shaped elements—so-called dilators—between the two vertebral bodies, so as to spread them apart step-by-step. Dilators, each with a 1 mm larger diameter, in alternation left and right, are here attached posteriorly. After the maximum possible spread has been reached, the dilators are replaced by the above-mentioned cortico-spongious bone.

This known technique has the disadvantage that the bone is difficult to handle and to bring into the proper position, corrections being nearly impossible. Another disadvantage of this technique is that a rectangular or cylindrical recess must be punched and/or milled out of the intervertebral space, so that the bone plugs can be inserted between the originally concave sides of the adjoining vertebral bodies. This is complicated and furthermore results in damage to the vertebral body.

WO89/12431 discloses an implant for the intervertebral space. This implant has the shape of a hollow cylinder and is perforated on all sides. It can be closed from the manipulation side by means of a screw cover. Bone mass which may possibly be inserted into the cylinder cavity cannot be compressed and, in addition, the small perforations—intended only for the bone to grow in—would make pressing out the bone mass impossible.

WO90/000037 discloses a square implant, perforated on all sides, for the intervertebral space. It has a screw/wedge mechanism mounted in its interior, by means of which four claws can be run out both on the top and on the bottom. So that bone mass can be filled into this implant pre-operatively, the screw/wedge mechanism first must be unmounted and then must be remounted again, which would be very complicated. But even in such a case, the bone mass could not exit from the implant because, on the one hand, the existing, relatively large slits would be closed by the run-out claws and, on the other hand, the small perforations are unsuited for this.

PCT/CH94/00184 to BECKERS describes an implant whose specific shape and mode of insertion makes possibly an extremely stable clamping between the vertebral bodies, without thereby damaging the surface of the bony cover plate of the vertebral bodies.

The starting point of this implant is a certain shape of the cover plates which belong to the two adjoining vertebra and which bound the intervertebral space. However, in reality the geometry of the cover plate varies from patient to patient. As a result, the contact between th e bone material pt into the implant and the cover plates is not always optimal. Depending on circumstances, this can delay bone healing. The invention provides a remedy for this.

SUMMARY OF THE INVENTION

It is the object of the invention to provide an implant for the intervertebral space, such that the bone mass introduced therein—after implantation—can be compressed and can be pressed out against the treated cover plates of the adjoining vertebra, whose cartilage has been re moved. In this way, the cavity resulting from an anatomical mismatch is filled up with bone mass.

The invention achieves its set objective by means of ar implant which has the features a frame which is closed at the side but is open without restriction on the top and bottom, and which has an anterior lead-in face and a posterior manipulation face, with upper and lower boundaries of the frame being convex in shape, so that the implant has a overall lens shape. The inner cavity of the implant is open without restriction on the top and bottom, and is filled with a compressible material. Also, the posterior manipulation face includes an aperture which allows the introduction of a compression element which is used to force the compressible material out from the cavity. This implant can be manipulated by use of an instrument having a sleeve which includes means for exerting torque on the implant, and two inserts which engage each other concentrically and which are connected to the compression element in such a fashion that forces are exerted in the direction of the longitudinal axis of the implant by one insert, and about the longitudinal axis by the other insert.

The compression element which can be inserted into the inventive implant can be gripped by a tool, so that, if the implant is appropriately designed, an external force and a torque can be exerted on the implant relatively easily, by way of the compression element. This makes it possible to insert the implant, together with the compression element, into the intervertebral space, to remove them, aid to manipulate them individually or jointly.

The apparatuses which allow a tool to exert a grip can be designed as attachment points in such a fashion that a rotational force and/or an axial force and/or a lateral force can be exerted on the compression element and through this on the implant itself.

In an advantageous embodiment of the compression element and of the implant in an appropriately designed instrument, these attachment points are constructed at least in such a way that they make it possible to exert a rotational force on the compression element and on the implant itself.

BRIEF DESCRIPTION OF THE DRAWINGS

To elucidate the invention better, several examples of advantageous embodiments will be described below, with reference to the appropriate drawings, but the invention is not limited to these drawings wherein.

DETAILED DESCRIPTION OF THE PREFERRED EMBODIMENT

The invention and modifications thereof will be explained in more detail below by means of partially schematic representations of several embodiments.

Figure 1:
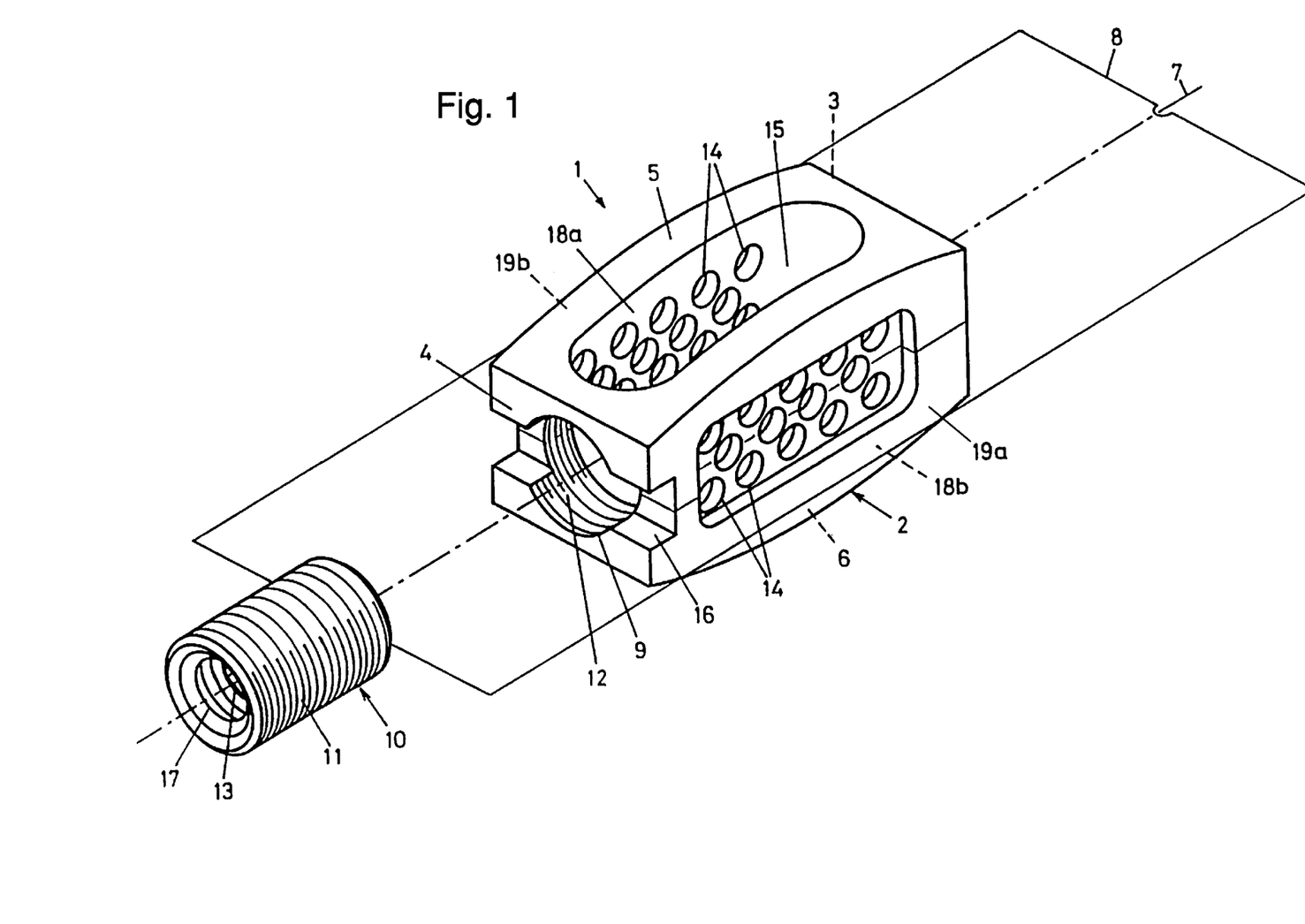
FIG. 1 shows a a perspective view of the implant with its compression element.

The implant 1 shown in FIG. 1 essentially consists of a frame 2, which is laterally closed but which is open without restriction on the top and bottom, and which has an anterior insertion face 3 and a posterior manipulation face 4.

The longitudinal axis 7 of the implant 1 is the mid-perpendicular on the anterior insertion face 3 and the posterior manipulation face 4. The mid-plane 8 of the implant 1 is defined by the longitudinal axis 7 of the implant 1 and the mid-perpendicular to the lateral faces 19a, 19b of the frame 2.

The posterior manipulation face 4 of the frame 2 has an aperture 9, into which a compression element 10 can be inserted. The compression element 10 preferably is a screw with a thread 11 and a hexagon socket 13. This screw is inserted into the aperture 9, thread 11 mating with internal thread 12 of aperture 9, before the implant 1 is inserted into the intervertebral space.

The frame 2, which is formed by the faces 3, 4 and the lateral walls 19a, 19b, encloses a cavity 15, which can be filled with a compressible mass, preferably consisting of autologous bone material, and which can be compressed in situ by means of the compression element 10, after the implant 1 has been inserted into the intervertebral space.

Implant 1 has a P value of about 0.5 to 1.5 mm, wherein P is defined as FT/O, where F is the cross sectional area F of the aperture 9, T is the maximum possible penetration depth of the compression element 10 into the inner cavity 15, and O is the reciprocal of the sum of the areas of the two openings 18a, 18b in the upper and lower boundaries 5, 6 of the frame 2. Preferably, the P value is between 0.6 and 0.9 mm.

The lateral walls 19a, 19b of the implant 1 shown in FIG. 1 have perforations 14, through which the bone can grow into the implant 1. The upper and lower boundaries 5, 6 of the frame 2 are provided with apertures 18a, 18b. The area of the apertures 18a, 18b preferably represents 40 to 60%, and most preferably 45 to 55%, of the entire cross sectional area of the implant 1.

The transverse slot 16, which is situated in the posterior manipulation face 4, serves as an apparatus for gripping the implant 1 by an instrument. The transverse slot 16 shown here makes it possible to apply a rotational torque, via the instrument, directly on the implant 1.

Figures 2, 3:
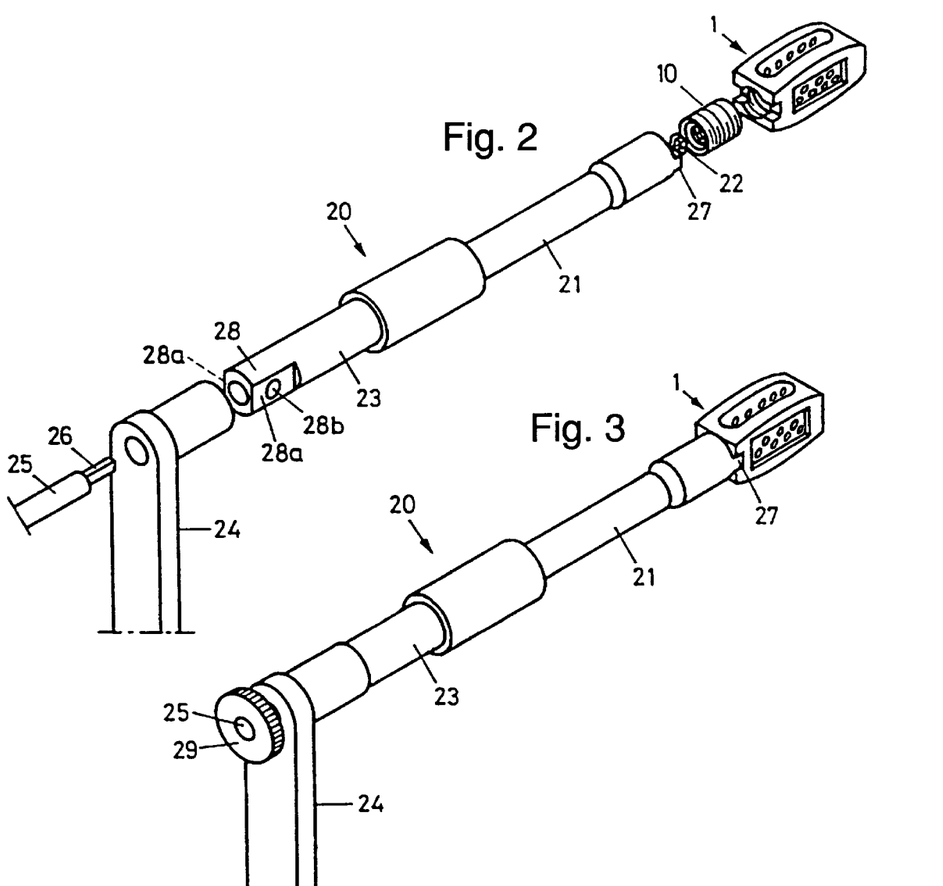
FIG. 2 shows an exploded view of an instrument suited for manipulating the implant of FIG. 1.
FIG. 3 shows a a perspective view, of the instrument of FIG. 2.

FIG. 2 shows the implant 1 together with the compression element 10 and the instrument 20. The instrument 20 makes it possible to manipulate simultaneously the implant 1 and the compression element 10. The instrument 20 essentially consists of a sleeve 21, a tube-like insert 23, a handle 24, and another insert 25. The sleeve 21 has an apparatus 27 which fits into the slot 16 of the implant 1. This slot 16 makes it possible to transmit a torque from the instrument 20 directly to the implant 1. The insert 23 is pushed into the sleeve 21 and is connected thereto in a rotationally stable fashion. Its front end has an apparatus 22 so as to connect it to the compression screw 10 in a manner that is resistant to tension and compression (see FIG. 4). The posterior end 28 of the insert 23 has a geometry which makes possible a rotation-, tension-, and compression-stable connection between the insert 23 and the handle 24. Rotational stability is assured by the two faces 28a. Two co-lateral balls, situated in the handle 24, are pressed into the co-lateral bores 28b when the handle 24 is pushed on the insert 23, and they thus make it possible to apply stretching and compressing forces, via the compression element 10, to the implant 1. The second insert is pushed on only after the apparatus 22 has already clicked into the compression element 10. It presses the apparatus 22 apart, and in this way prevents the connection from loosening up when forces appear in the longitudinal axis of the implant 1. The second insert 25, shown in FIG. 2, has a hexagon bolt 26 in front, which is inserted into the hexagon socket of the compression element 10. This hexagon bolt 26 makes it possible to turn the compression element 10 in and out, since it is designed as a screw, and thus makes it possible to compress the fill mass in the implant 1. The insert 25 is operated by a small hand wheel 29, shown in FIG. 3

FIG. 3 shows the instrument 20, in its mounted state, with the insert 25 in the grip and with the mounted hand wheel 29.

Figure 4:
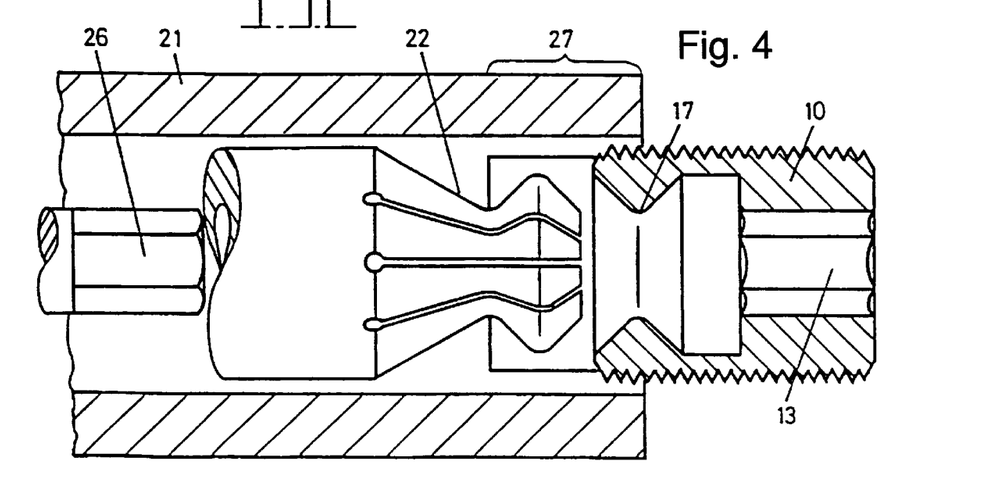
FIG. 4 shows a partial longitudinal section through the instrument of FIG. 3, in the transition region between the instrument and the compression element of the implant.

FIG. 4 shows the lower part of the instrument 20 directly before its end 23 is clicked into the compression element 10. The end 23 resembles a collet chuck and has at least one slot. After it has been clicked in, the insert 25 is pushed into the insert 23 far enough so that the hexagon bolt 26 penetrates completely into the hexagon socket 13 of the compression element 10. In this position, the insert 25 prevents the collet chuck 22 from being compressed Due to the flange 17, the connection between the instrument 20 and the compression element 10 can now accept forces in the longitudinal direction of the implant 1. Once it is connected to the instrument 20, the compression element 10 can be turned relative to the instrument 20 by means of the insert 25. As already mentioned, the instrument 20 is itself connected to the implant 1 by means of the apparatus 27, in a rotationally stable manner. This now makes it possible to turn the compression element 10 into the implant 1 by means of the insert 25, and thus to compress the fill mass and to press it through the apertures 18a, 18b in the upper and lower convex boundaries 5, 6 of the frame 2, against the cover plates 130 of the upper and lower adjoining vertebral bodies 100.

The connection between the instrument 20, shown in FIGS. 2 and 3, and the implant 1, shown in all the figures, is made as follows:

Clicking the collet chuck 22 into the compression element 10

Pushing in the insert 25 until its hexagonal bolt 26 has completely disappeared in the hexagonal socket 13 of the implant 1

Inserting the apparatus 27 of the instrument 20 in to the apparatus 16 of the implant 1

Inserting the compression element 10 into the implant 1 until its most forward part is flush with the in side of the frame 2 of the implant 1.

The implant 1 or the compression element 10 can now be manipulated with the instrument 20 as needed: insertion, rotation, and compression. The connection is designed in such a way that especially torques about and forces along the longitudinal axis 7 can be exerted on the compression element 10 through the instrument 20 and can be exerted on the implant 1 through the compression element 10. The mass, preferably consisting of autologous bone, is filled in only after the instrument 20 has been connected to the implant 1 and before the implant 1 has been inserted into the intervertebral space.

Figure 5:
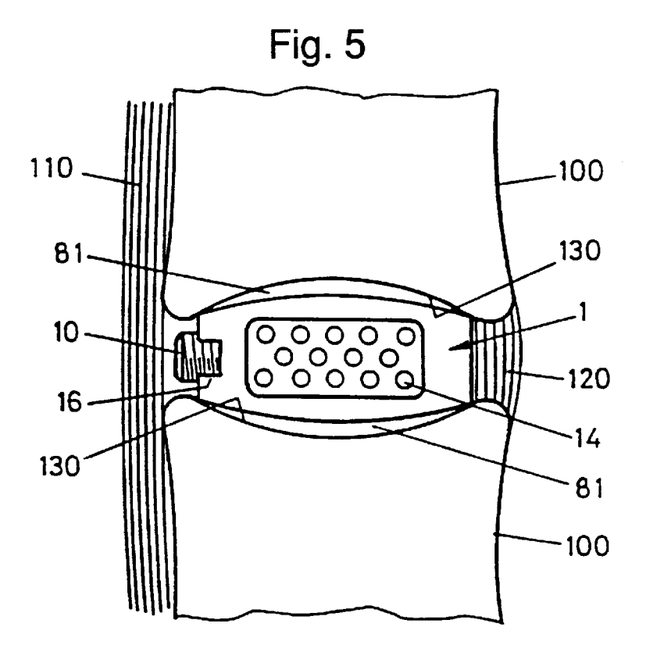
FIG. 5 shows a longitudinal section through an implant of FIG. 1, inserted into the intervertebral space, before the bone mass has been compressed.
Figure 6:
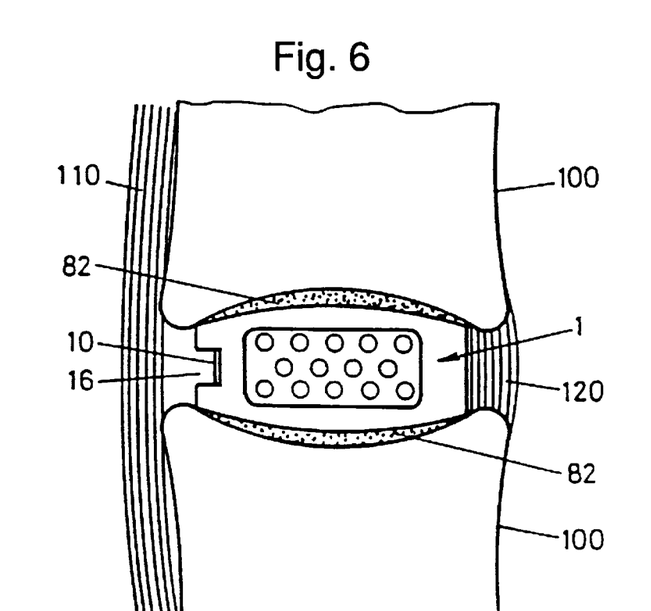
FIG. 6 shows a longitudinal section of an implant according to FIG. 1, inserted into the intervertebral space, after the bone mass has been compressed.

It will now be explained, with reference to FIGS. 5 and 6, how the fill mass is compressed and is pressed into the cavity between the implant 1 and the bone. As a preliminary, the implants 1, in transverse position, are inserted from posterior left and right, past the dura 110, by means of the instrument 20 (two implants per vertebral segment that is to be fused). They are then set upright about their longitudinal axis 7. Toward anterior, they are held by the remaining annulus 120 of the intervertebral disk. Toward posterior, they are generally stabilized by an additional posterior pedicle fixation system. FIGS. 5 and 6 show one of these two implants 1 after it has been inserted and set upright, The compression element 10 in FIG. 5 is still in its initial position, i.e. it is still turned in so far that the implant 1 can be manipulated through the compression element 10, by means of the instrument 20, without already compressing the fill mass.

For the sake of clarity, the instrument 20, which is fixedly connected to the implant 1, has not been shown in the drawing. The anatomical structures shown in FIGS. 5 and 6 show a certain discrepancy between the upper and lower boundary 5 and 6 of the implant 1 and the cover plates 130 of the adjoining vertebral bodies 100. The objective now is to turn in the compression element by means of the insert 25 until the fill mass 82, emerging on the top and bottom, has filled up the cavity 81 between the implant 1 and the bone.

FIG. 6 shows the implant 1 after the compression element 10 has been turned in. The cavity 81 is filled completely with the emerging fill mass 82.

What is claimed is:

1. An implant for an intervertebral space comprising a compression element and a frame having closed sides, and a top and bottom which are open, said frame defining an inner cavity provided with an anterior lead-in face and a posterior manipulation face, the frame further having a longitudinal axis extending from the anterior face to the posterior face, wherein the inner cavity is open without restriction at the top and bottom and contains compressible material therein, and the posterior manipulation face of the frame is provided with an aperture shaped for the introduction of the compression element to force the compressible material out of the inner cavity through the top and bottom of the frame, wherein the compression element is insertably adjustable into the cavity.

2. The implant of claim 1, wherein the aperture is shaped so that the compression element can be moved unidirectionally in the direction of the longitudinal axis toward the anterior lead-in face.

3. The implant of claim 1, wherein the aperture has an inside thread so as to accept a rotationally symmetric compression element with a corresponding outside thread.

4. The implant of claim 1, wherein said compressible material is a mixture of bone chips for encouraging bone formation.

5. The implant of claim 1, wherein the frame has upper and lower boundaries convexly curved about an axis transverse to the longitudinal axis so that the implant has an overall lens shape substantially corresponding to the intervertebral space in which the implant is to be inserted.

6. The implant of claim 1, wherein the upper and lower boundaries have apertures which are open without restriction and which have an area representing 40 to 60% of the entire cross sectional area of the implant.

7. The implant of claim 1, wherein the upper and lower boundaries have apertures which have an area representing 45 to 55% of the entire cross sectional area of the implant.

8. The implant assembly of claim 1, wherein the upper and lower boundaries are convexly curved about a plane transverse to the longitudinal axis.

9. The implant of claim 1, wherein the frame has means for attaching a manipulation instrument wherein, when the manipulation instrument is attached to the means of the frame, the frame and the compression element can be positionally adjusted as a unit within the intervertebral space by the manipulation instrument.

10. The implant of claim 9, wherein the compression element includes means for exerting a rotational torque against the frame, while said frame is held in position independently with the attached manipulation instrument.

11. The implant of claim 10, wherein the means for exerting the rotational torque upon the compression element comprises a hexagonal socket and wherein the compression element is a cylindrical screw with outer threads, said screw having on one end the hexagonal socket.

12. The implant of claim 9, wherein the the means for attaching the mating manipulation instrument is a horizontal slot on the posterior manipulation face.

13. The implant of claim 10, wherein the rotational torque exerting means comprises a bore having a complex bore profile and wherein the compression element is a cylindrical screw having outer threads.

14. The implant of claim 13, wherein the complex bore profile, viewing the screw from a mid-line, horizontal cross-sectional perspective, has a plurality of bore portions to provide a variable bore diameter that begins at a posterior face of the screw, with the first bore portion first increasing in size, then decreasing in size and finally maintaining a constant diameter, a second bore portion maintaining a constant diameter, and the second bore portion connected to the first bore portion, the second bore portion comprising a hexagonal socket having a cross-sectional diagonal width which is smaller than the smallest diameter of the first bore portion.

15. An implant for an intervertebral space comprising a frame having closed sides, and an open top and bottom, said frame defining an inner cavity provided with an anterior lead-in face and a posterior manipulation face, the frame further having a longitudinal axis extending from the anterior face to the posterior face and upper and lower boundaries convexly curved about an axis transverse to the longitudinal axis so that the implant has an overall lens shape substantially corresponding to the intervertebral space into which the implant is to be inserted, wherein the inner cavity is open without restriction at the top and bottom, wherein the posterior manipulation face of the frame is provided with an aperture, and wherein the implant has a P value of about 0.5 to 1.5 mm, wherein P is defined as FT/O, where F is the cross sectional area F of the aperture, T is the maximum possible penetration depth of the compression element into the inner cavity, and O is the reciprocal of the sum of the areas of the two openings in the upper and lower boundaries of the frame.

16. The implant of claim 15, wherein the P value is between 0.6 and 0.9 mm.

17. An implant for an intervertebral space comprising: a compression element that has a bore with a flange; and a frame having closed sides and a top and bottom which are open without restriction, said frame defining an inner cavity provided with an anterior lead-in face and a posterior manipulation face, the frame further having a longitudinal axis extending from the anterior face to the posterior face and upper and lower boundaries so that the implant has an overall lens shape substantially corresponding to the intervertebral space in which the implant is to be inserted, wherein the inner cavity is open without restriction at the top and bottom and includes compressible material therein, and wherein the posterior manipulation face of the frame is provided with an aperture shaped for the introduction of the compression element in order to force compressible material out of the inner cavity through the top and bottom of the frame.

18. The implant of claim 17, wherein the posterior manipulation surface includes a transverse slot, the aperture includes a thread therein, and the compression element includes a hexagonal socket, so that the implant and the compression element can be manipulated simultaneously by means of an instrument.

19. The implant assembly of claim 13, wherein the closed sides are provided with apertures shaped to permit bone ingrowth, the open top and bottom of the frame each being larger than the apertures in the lateral walls.

* * * * *

UNITED STATES PATENT AND TRADEMARK OFFICE
CERTIFICATE OF CORRECTION

PATENT NO. : 6,059,829
DATED : May 9, 2000
INVENTOR(S) : Fridolin SCHLÄPFER et al.

It is certified that error appears in the above-identified patent and that said Letters Patent is hereby corrected as shown below:

On the title page at "[73] Assignee": change the name of the assignee to --Synthes (U.S.A.), Paoli, PA--.

Signed and Sealed this

Twenty-second Day of May, 2001

Attest:

NICHOLAS P. GODICI

*Attesting Officer*     *Acting Director of the United States Patent and Trademark Office*

UNITED STATES PATENT AND TRADEMARK OFFICE
CERTIFICATE OF CORRECTION

PATENT NO. : 6,059,829
DATED : May 9, 2000
INVENTOR(S) : Fridolin Schläpfer et al.

It is certified that error appears in the above-identified patent and that said Letters Patent is hereby corrected as shown below:

Column 3,
Line 28, delete "the reciprocal of".

Column 5,
Line 20 (claim 1, line 8), between "contains" and "compressible", insert -- non-gaseous --.
Line 25 (claim 1, line 13), after "of the frame" and before the ",", insert -- after the implant has been inserted into the intervertebral space --.
Line 41 (claim 6, line 1), after "wherein the", insert -- frame includes --.
Line 42 (claim 6, line 2), after "boundaries", insert -- that --.
Line 43 (claim 6, line 3), after "tion and which", insert -- apertures --; and after "have", delete "an" and insert -- a combined --.
Line 45 (claim 7, line 1), after "wherein the", insert -- frame includes --.
Line 46 (claim 7, line 2), after "boundaries", insert -- that --; after "have apertures which", insert -- apertures --; and after the second occurrence of "have", delete "an" and insert -- a combined --.
Line 48 (claim 8, line 1), after "wherein the", insert -- frame includes --.
Line 49 (claim 8, line 2), after "and lower boundaries", insert -- which --.
Line 51 (claim 9, line 1), delete "The implant of claim 1," and insert -- An implant for an intervertebral space comprising a compression element and a fram having closed sides, and a top and bottom which are open, said frame defining an inner cavity provided with an anterior lead-in face and a posterior manipulation face, the frame further having a longitudinal axis extending from the anterior face to the posterior face, wherein the inner cavity is open without restriction at the top and bottom and contains compressible material therein, and the posterior manipulation face of the fram is provided with an aperture shaped for the introduction of the compression element to force the compressible material out of the inner cavit through the top and bottom of the frame, wherein the compression element is insertabley adjustable into the cavity, and --.

UNITED STATES PATENT AND TRADEMARK OFFICE
CERTIFICATE OF CORRECTION

PATENT NO. : 6,059,829  
DATED : May 9, 2000  
INVENTOR(S) : Fridolin Schläpfer et al.

Page 2 of 2

It is certified that error appears in the above-identified patent and that said Letters Patent is hereby corrected as shown below:

Column 6,
Line 1 (claim 12, line 1), delete the second occurrence of "the"
Line 31 (claim 15, line 15), delete "F".
Line 33 (claim 15, line 17), delete "the reciprocal of".
Line 59 (claim 19, line 1), delete "The implant assembly of claim 13," and insert
-- An implant for an intervertebral space comprising a compression element and a fram having closed sides, and a top and bottom which are open, said frame defining an inner cavity provided with an anterior lead-in face and a posterior manipulation face, the frame further having a longitudinal axis extending from the anterior face to the posterior face, wherein the inner cavity is open without restriction at the to and bottom and contains compressible material therein, and the posterior manipulation face of the frame is provided with an aperture shaped for the introduction of the compression element to force the compressible material out of the inner cavity through the top and bottom of the frame, wherein the compression element is insertably adjustable into the cavity, and --.

Signed and Sealed this

Ninth Day of October, 2001

*Attest:*

NICHOLAS P. GODICI  
*Attesting Officer*   Acting Director of the United States Patent and Trademark Office

UNITED STATES PATENT AND TRADEMARK OFFICE
CERTIFICATE OF CORRECTION

PATENT NO.    : 6,059,829
DATED         : May 9, 2000
INVENTOR(S)   : Fridolin Schläpfer et al.

It is certified that error appears in the above-identified patent and that said Letters Patent is hereby corrected as shown below:

<u>Column 3,</u>
Line 28, delete "the reciprocal of".

<u>Column 5,</u>
Line 20, between "contains" and "compressible", insert -- non-gaseous --.
Line 25, after "of the frame" and before the ",", insert -- after the implant has been inserted into the intervertebral space --.
Line 41, after "wherein the", insert -- frame includes --.
Line 42, after "boundaries", insert -- that --.
Line 43, after "tion and which", insert -- apertures --; and after "have", delete "an" and insert -- a combined --.
Line 45, after "wherein the", insert -- frame includes --.
Line 46, after "boundaries", insert -- that --; after "have apertures which", insert -- apertures --; and after the second occurrence of "have", delete "an" and insert -- a combined --.
Line 48, after "wherein the", insert -- frame includes --.
Line 49, after "and lower boundaries", insert -- which --.
Line 51, delete "The implant of claim 1," and insert -- An implant for an intervertebral space comprising a compression element and a frame having closed sides, and a top and bottom which are open, said frame defining an inner cavity provided with an anterior lead-in face and a posterior manipulation face, the frame further having a longitudinal axis extending from the anterior face to the posterior face, wherein the inner cavity is open without restriction at the top and bottom and contains compressible material therein , and the posterior manipulation face of the frame is provided with an aperture shaped for the introduction of the compression element to force the compressible material out of the inner cavity through the top and bottom of the frame, wherein the compression element is insertably adjustable into the cavity, and --.

UNITED STATES PATENT AND TRADEMARK OFFICE
CERTIFICATE OF CORRECTION

PATENT NO. : 6,059,829
DATED : May 9, 2000
INVENTOR(S) : Fridolin Schläpfer et al.

It is certified that error appears in the above-identified patent and that said Letters Patent is hereby corrected as shown below:

<u>Column 6,</u>
Line 1, delete the second occurrence of "the".
Line 31, delete "F".
Line 33, delete "the reciprocal of".
Line 59, delete "The implant assembly of claim 13," and insert -- An implant for an intervertebral space comprising a compression element and a frame having closed sides, and a top and bottom which are open, said frame defining an inner cavity provided with an anterior lead-in face and a posterior manipulation face, the frame further having a longitudinal axis extending from the anterior face to the posterior face, wherein the inner cavity is open without restriction at the top and bottom and contains compressible material therein, and the posterior manipulation face of the frame is provided with an aperture shaped for the introduction of the compression element to force the compressible material out of the inner cavity through the top and bottom of the frame, wherein the compression element is insertably adjustable into the cavity, and --.

This certificate supersedes Certificate of Correction issued October 9, 2001.

Signed and Sealed this

Twentieth Day of August, 2002

*Attest:*

JAMES E. ROGAN
*Attesting Officer*    *Director of the United States Patent and Trademark Office*